United States Patent [19]

Lenczyk

[11] Patent Number: 5,047,209
[45] Date of Patent: Sep. 10, 1991

[54] CONTROL SYSTEM FOR THE QUANTIFICATION OF THE QUALITY OF FLUIDIZATION USING A THERMOCOUPLE

[75] Inventor: John P. Lenczyk, Akron, Ohio
[73] Assignee: The B. F. Goodrich Company, Akron, Ohio
[21] Appl. No.: 156,515
[22] Filed: Feb. 16, 1988

Related U.S. Application Data

[62] Division of Ser. No. 848,102, Apr. 4, 1986, Pat. No. 4,740,643.
[51] Int. Cl.$^5$ .................. C07C 17/156; G01N 31/10; G05D 7/00
[52] U.S. Cl. .................. 422/62; 422/110; 422/111; 422/140; 436/55; 570/243
[58] Field of Search .................. 165/104.16; 122/4 D; 431/7, 170; 110/245; 34/57 A; 422/140, 145, 146, 62, 109, 110, 111; 570/245, 243; 436/55

[56] References Cited

U.S. PATENT DOCUMENTS

| | | | |
|---|---|---|---|
| 3,350,915 | 11/1967 | Staffin | 164/104.16 |
| 3,892,816 | 7/1975 | Kister | 570/245 |
| 4,226,798 | 10/1980 | Cowfer et al. | 422/110 |
| 4,329,527 | 5/1982 | Kühn et al. | 570/245 |
| 4,339,620 | 7/1982 | Cowfer et al. | 570/243 |
| 4,446,249 | 5/1984 | Eden | 502/225 |
| 4,708,812 | 11/1987 | Hatfield | 427/213.31 |
| 4,801,572 | 1/1989 | Hsieh | 502/306 |

FOREIGN PATENT DOCUMENTS 700607  12/1964  Canada .................. 260/654

*Primary Examiner*—Robert J. Warden
*Assistant Examiner*—Kimberly A. Trautman
*Attorney, Agent, or Firm*—Alfred D. Lobo; Nestor W. Shust; Thoburn T. Dunlap

[57] ABSTRACT

The operation of a fluid-bed reactor in which the catalyst has a proclivity to stickiness deleterious to efficiently carrying out a reaction of the gaseous components fed to the reactor, is controlled by monitoring the fluctuations in temperature at various locations in the bed, and computing the standard deviation of temperature at predetermined intervals of time. When the fluid-bed consists essentially of a supported catalyst performing at peak efficiency, near which it has a proclivity to "stickiness", slight fluctuations, less than 1° F., of operating temperature are correlatable to the quality of fluidization and the risk of an uncontrollable upset in the reactor.

2 Claims, 2 Drawing Sheets

CONTROL SYSTEM FOR THE QUANTIFICATION OF THE QUALITY OF FLUIDIZATION USING A THERMOCOUPLE

This is a division, of application Ser. No. 06/848,102, filed Apr. 4, 1986, now U.S. Pat. No. 4,740,643.

BACKGROUND OF THE INVENTION

This invention relates to the operation of a fluidized-solid bed ("fluid-bed") reactor in which an exothermic chemical reaction occurs at elevated temperature and pressure More particularly this invention relates to a process for monitoring whether a fluid-bed supported catalyst with a peculiar proclivity to "stickiness" is performing satisfactorily in a reactor sought to be operated at optimum conditions, namely those at which maximum conversion to desired products is obtained at minimum cost.

"Stickiness" or "tackiness" which is not necessarily viscosity, as conventionally defined, is attributed to the degree of particle-to-particle agglomeration, viscosity or resistance to movement or separation of constituent particles. Stickiness of a supported catalyst is dependent upon the pressure and temperature of the catalytic reaction, the adsorptive quality of the catalyst, the amount and distribution of active ingredient on the surface, the number of active sites available on the catalyst and the manner and degree of their utilization, and the quantity and physico-chemical properties of the reactants and reaction products in the fluid-bed. The problems associated with operating a fluid-bed with catalysts having such characteristics are discussed in U.S. Pat. No. 4,226,798 which is incorporated by reference thereto as if fully set forth herein.

Catalyst particles which exhibit a tendency to stick to one another include supports on which are deposited "soft" elements of Group I, V, VI and VIII of the Periodic Table, and compounds thereof Most susceptible to a change in consistency are supported catalysts on which are deposited compounds of copper, iron, bismuth, antimony and the like and which additionally may be promoted by the rare earth elements and elements of Groups II, IV and VII.

To obtain a good indication of what is widely believed to be the precise condition of an operating fluid-bed, it is conventional to monitor the bed height, corresponding bed density and pressure drop continuously across the bed, and to record an hourly (or half-hourly) moving average bed height, bed density and pressure drop, and thus estimate the efficiency of the overall reaction. By "efficiency" I refer to conversion of one or more feed components to desirable products at minimum cost.

The method of selecting operation of a fluid-bed reactor and the apparatus for doing so in the '798 patent resulted from recognition of the inadequacy of prior art methods to warn of an impending "upset" whatever its cause, and particularly because measurements of bed height and pressure drop provided inadequate information of equivocal probative value, too late to avoid reaching the "point-of-no-return" or the "inversion point" of the fluid-bed. It is at this point that a peak viscosity is reached which is higher than the usual viscosity at which optimum operation of the bed is achieved.

As pointed out in the '798 patent, time is important because in an operating fluid-bed having a quantum of stickiness typical for a particular catalyst, a process upset can change the stickiness quite suddenly, and if not countered quickly, will provide no alternative but to shut the reactor down. Though the '798 invention is effective to operate a reactor with excellent control, it is not particularly suited for facile and routine use by a typical operator in the plant. For obvious reasons, it is not convenient to operate a laboratory reactor in which the fluid-bed is provided by a slipstream from the plant reactor. Even if the mechanical problems of introducing the slipstream into the laboratory reactor, and operating the torsional pendulum are disregarded, it is evident that the precise viscosity of the slipstream, after it is transferred from the plant reactor to the laboratory reactor are affected to some degree. It is more advantageous to make the viscosity measurements in situ, while the plant reactor is operating, except that methods for doing so, to date have proven inadequate.

The size of bubbles in a fluid-bed have been measured to determine temperature, as a function of time, at different points between which a temperature gradient exists, using a minute thermocouple. See "Measurement of Temperature in Bubble and Emulsion Phases" by Yamazaki, M. et al *Kagaku Kogaku Rombunshu* 3(3), 261(5). But this work was not related to exothermic reactions which take place in the emulsion phase since a bed operating with the reaction in the emulsion phase should show no measurable change in temperature, because the mixture is perfect and the bubbles are extremely small.

In accordance with the two-phase model of aggregative fluidization in which a fluid bed consists of an emulsion phase and a bubble phase, the emulsion phase consists of a uniform continuum of particles through which the fluid velocity is equal to the minimum fluidizing velocity, and the voidage is the minimum voidage; and, each particle is considered as free of contact from adjacent particles. Presumably, no entrainment occurs at incipient fluidization.

The point of incipient fluidization is generally defined as the lowest superficial fluid velocity at which the pressure drop across the bed (at its loosest packed density), multiplied by the total area of the bed, equals the weight of the bed charge. At this point a slight increase of fluid velocity should cause an incremental lifting or expansion of the bed and create the dense "fluid" state in which the bed particles rest more upon a cushion of gas (the fluid) than directly upon each other. A change in viscosity of the bed will affect the bed height. Prior to fluidization, the particles present a conventional fixed-bed configuration.

In another study, the static pressure distribution in the fluid-bed was measured and the behavior of the bubbles investigated by use of a hot-wire anemometer (probe). See "Behavior of Bubbles and Circulating Flow of the Emulsion Phase in a 60 cm diameter Fluidized Catalyst Bed" by Tsutsui, Toshio et al *Kagaku,* supra, 6(5), 501–7. But the flow of bubbles in an operating reactor is of little interest in this invention, since such flow does not determine optimum operating conditions for the bed.

In still another study it was recognized that the temperature within the larger bubbles in a fluid-bed was lower than that in the emulsion phase. But the significance of such a temperature difference at any predetermined location within the bed could only be realized if one was confronted with a catalyst having the peculiar property of "a proclivity to stickiness", and one was told that the temperature at that location would actually fluctuate meaningfully within a narrow range less than 1° F. Since operation of the fluid-bed was deemed to be isothermal, there was neither reason to expect such a fluctuation nor to attribute any particular significance to such a slight fluctuation if it did exist The experimental error in the measurement of temperature with a thermocouple often exceeds 0.5° F. This invention derives from having (i) used a thin thermocouple, that is, smaller in diameter than that of bubbles which will presage stickiness, and (ii) having been able to measure the slight fluctuations in temperature and identifying their significance relative to the quality of fluidization.

SUMMARY OF THE INVENTION

It has been discovered that slight fluctuations, less than 1° F., of operating temperature within an operating fluid-bed reactor containing a supported catalyst performing at peak efficiency, near which it has a proclivity to "stickiness", are correlatable to the quality of fluidization and the risk of an uncontrollable upset in the reactor.

It is therefore a general object of this invention to provide a fluid-bed reactor operating at elevated temperature and containing a finely divided catalyst which catalyzes a reaction between gaseous reactants; the reaction changes the viscosity of the catalyst at operating conditions as a function of the ratio of the reactants; the particular improvement comprises, at least one thermocouple means, located at a preselected location within the bed, including a sheath having a diameter smaller than that of an average bubble present when the bed approaches peak viscosity, and adapted to measure fluctuations in the range from about 0.1° F. to about 0.5° F. of the temperature at the location; means to compute an average temperature at said location during a predetermined period of time; means to compute the standard deviation of temperature at said location within said period of time so as to quantify the quality of fluidization of said catalyst; and, means to control the ratio of said reactants to lower said standard deviation below a preselected numerical value.

It has more particularly been discovered that a single thin thermocouple no greater than 0.050 inch in diameter, placed at a predetermined location within an operating fluid-bed, can sense changes in temperature of less than 0.5° F., and that the magnitude of the fluctuations indicates the quality of fluidization; the smaller the fluctuation, the better the fluidization; bigger fluctuations indicate the presence of larger bubbles than are desirable for optimum performance. Thus the thermocouple directly measures the size of the bubbles, an increase in the size of the bubbles indicating an increase of stickiness of the catalyst. The usual viscosity near which the bed operates at optimum efficiency is thus indirectly quantified, as are changes in the viscosity.

BRIEF DESCRIPTION OF THE DRAWINGS

The foregoing and other objects and advantages of my invention will appear more fully from the following description, made in connection with the accompanying drawings of preferred embodiments of the invention, wherein like reference characters refer to the same or similar parts throughout the views and in which.

DETAILED DESCRIPTION OF PREFERRED EMBODIMENTS

Figure 1:
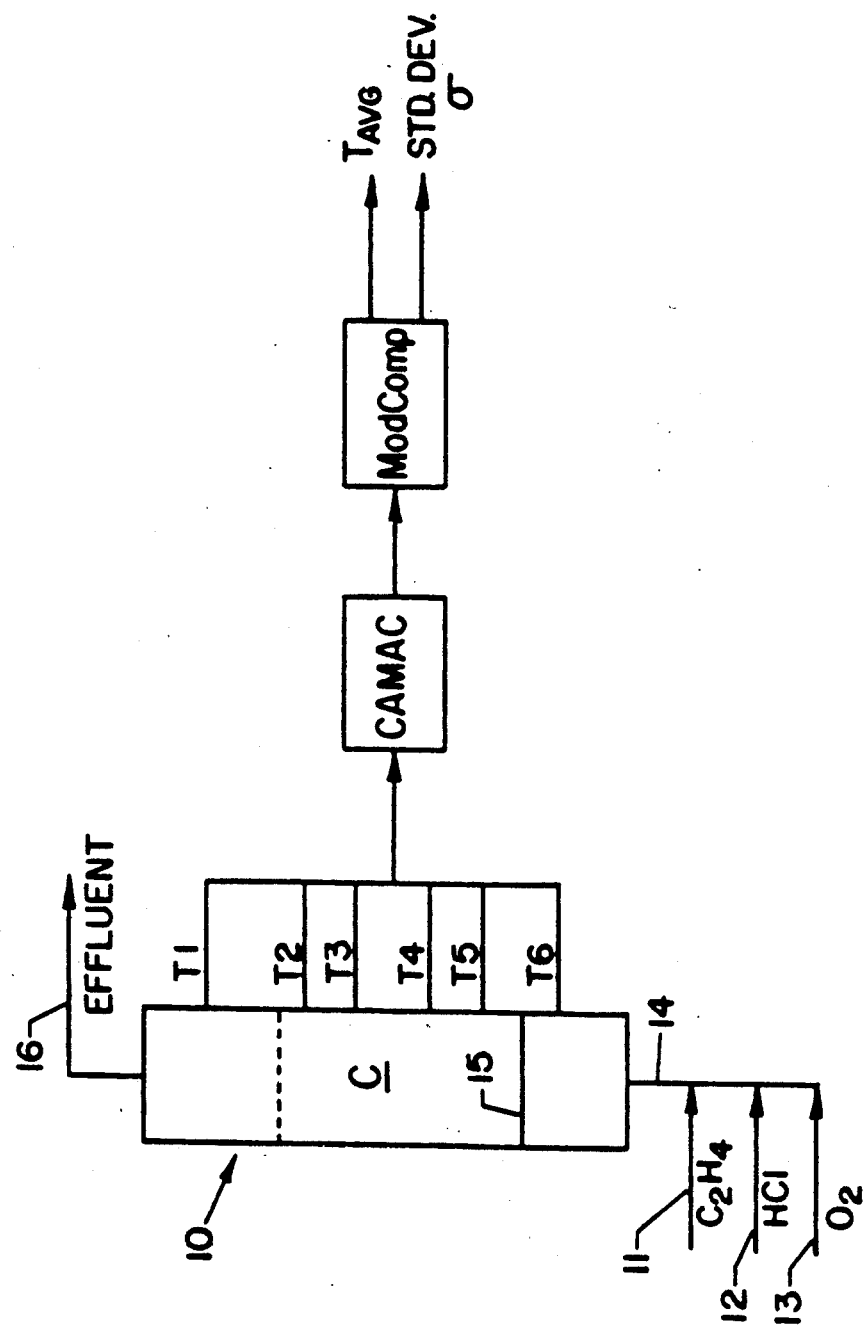
FIG. 1 is a schematic illustration of the apparatus used to monitor stickiness in a fluid-bed reaction.

In a particular preferred embodiment of this invention, a process for the oxyhydrochlorination of a monoolefin having from 2 to about 4 carbon atoms is carried out by reacting hydrochloric acid, oxygen and the monoolefin in a fluid-bed reactor. The reactor is equipped with appropriate auxiliary equipment, described in greater detail herebelow, to monitor indirectly the viscosity characteristics evidenced by a peculiar stickiness of the bed of catalyst. Such stickiness is noted in catalysts, of the type referred to hereinbefore, used to catalyze not only exothermic reactions but also some endothermic ones. Reaction typically occurs at a temperature above about 100° C. but below a temperature deleterious to the catalyst and at atmospheric or superatmospheric pressure. Measurement of the viscosity provides a good enough indication of stickiness, for the purposes of this invention, to monitor the efficiency of the operating bed.

To utilize this invention, it is sufficient that the viscosity of the catalyst be known to increase progressively as the efficiency of the bed approaches theoretical maximum for selected operating conditions. Clearly, maintaining maximum efficiency in a fluid-bed reactor is of most interest in a commercial reactor, and it is such a reactor to which the most preferred embodiment is directed. In a related use, the process of this invention may be used to select the most desirable catalyst from a number of catalysts with slightly varying specifications, or even from purportedly identical catalysts, by performance-testing them by the process described herein.

To oxyhydrochlorinate ethylene, a reactor is charged with a supported catalyst on which is deposited at least one element selected from the group consisting of elements of Groups I, V, VI and VIII of the Periodic Table and compounds thereof. The supported catalyst catalyzes the oxyhdrochlorination reaction. Meanwhile, the stickiness of the catalyst increases as conversion of the reactants to the desired product, namely ethylene dichloride (EDC), approaches the theoretical maximum.

In commercial operation, a fluid-bed reactor containing a copper chloride supported catalyst is used to produce 1,2-dichloroethane (EDC) in a process described in greater detail in U.S. Pat. No. 3,488,398 the disclosure of which is incorporated by reference thereto as if fully set forth herein. The support is attrition resistant silica, alumina, or the like. The overall reaction for converting ethylene to EDC proceeds as follows:

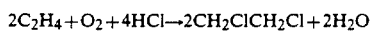

$$2C_2H_4 + O_2 + 4HCl \rightarrow 2CH_2ClCH_2Cl + 2H_2O$$

During the reaction some ethylene is converted to higher chloride-containing materials, and some is oxidized to CO and $CO_2$, so it is desirable to use a slight excess of ethylene and oxygen over stoichiometric. Thus, for every two moles of HCl, from about 1.02 to about 1.2 moles of ethylene, and from about 0.55 to about 0.9 mole of oxygen are preferably fed into the reactor to maximize utilization of HCl. The most preferred ratio of ethylene, HCl and oxygen is 1:1.9:0.8. Preferred feed components are contacted with the catalyst after it is fluidized and maintained at a temperature in the range from about 210° C. to about 240° C., in a plant reactor pressurized in the range from about 10 to 100 psig.

It is essential that a bare minimum of excess HCl be fed to the reactor, and that the maximum conversion of ethylene be obtained, both from the standpoint of effective use of the reactants as well as from the standpoint of minimizing the corrosive effects and purification problems in the recovery system. The catalyst is prepared by impregnating microspheroidal gel alumina with a solution of copper chloride, and drying it so that the amount of copper salt on the support is in the range from about 2.0 to about 12% by weight copper.

In a typical plant operation, the ratio of HCl to ethylene is monitored and maintained within the prescribed narrow limits. It is unnecessary to monitor bed height or bed density, though these may be monitored, if desired.

Referring now to FIG. 1 there is shown a schematic illustration of a fluid-bed reactor, indicated generally by reference numeral 10, to the bottom of which is fed predetermined amounts of ethylene, HCl, and oxygen through supply lines 11, 12 and 13 respectively. The lines are in open communication with a manifold 14 where the gases are mixed as they are introduced into the bottom of the reactor 10. The flow of ethylene is varied as dictated by measurements of standard deviation (std dev) to be made as will be described hereafter.

The bed of catalyst C is supported on a porous plate 15 beneath which the gases are introduced so that they can be more thoroughly mixed before flowing through the bed. A thermocouple T1 is provided above the disengagement zone of the bed, near the mouth of the effluent line 16; another thermocouple T6 is provided below the porous plate 15 to monitor the temperature in the bottom of the reactor where the gases are mixed. The physical dimensions of thermocouples T1 and T6 are not critical since measurements made by them are not related to stickiness of the catalyst in the fluid bed.

Thermocouple wells T2, T3, T4 and T5 are provided at various locations in the bed, and each well is fitted with a thermocouple having a sheath smaller in diameter than that of an average bubble which is formed when the bed approaches peak efficiency, generally no greater than 0.5" diameter, and preferably a 0.125" sheathed probe, each of which is connected to a thermocouple scanner in a scanning device adapted to convert analog signals of fluctuations in temperature to digital signals. The temperature is sensed a plurality of times each minute, by each thermocouple. The temperature sensed by each thermocouple, preferably 60 times per minute, is recorded in a separate channel. A commercially available device for doing so is a CAMAC communication device such as 525 Thermocouple/Temperature Monitor (Kinetic Systems, Inc.). The temperature data is transmitted to a storage device such as a ModComp Computer in which programs are stored to compute the average temperature at predetermined intervals, say every minute, and the std dev, and this information stored. The data for each channel is displayed, and printed if desired, as the average temperature $T_{avg}$ obtained from 60 readings, one each second for a minute, and the std dev $\sigma$. The readings are recorded at intervals of 30 min.

The std dev provides an immediate indication of the viscosity of the bed at the location of the thermocouple from which the std dev is derived. For this particular system, by a little trial and error, it is determined that when the std dev is less than 0.2, the efficiency of the bed is optimum; in the range from 0.2 to about 0.4 there is loss of performance because of an increase of viscosity; and when greater than 0.4, the bed is about to reach the point of no return.

The amount of ethylene flowed to the reactor is controlled by conventional flow control means according to the greatest std dev which approaches 0.4 for any of T2–T5. Thus the ratio of ethylene to oxygen is continuously controlled.

It will be evident to one skilled in the art that start-up of the reactor is done manually until it is operating with the desired optimum efficiency, at which time it is switched over to automatic control.

Referring again to the data provided for illustrative purposes, shows the beginning of the run, that is, soon after the reactor is placed on automatic control, until about 10 hr of operation. The channels for each of the thermocouple are listed across the top f the page. It is seen that T1 in channel 1 is defective, as evidence by the erratic numbers, including negative ones, recorded For most of the first hour, T6 in channel 6 is erratic but is then corrected. The data continues a record of the run after 1400 min to the end when, after more than 2000 min the reactor is shut down. At 1883 min approaches it is seen that T3 suddenly registers a std dev of 1.001 which is soon corrected to 0.210, but T5 registers a std dev of 1.048. Then T3 and T5 are both corrected but at 1973 T3 again registers 1.398, which though soon corrected finds T4 registering 1.103 at 2003 min. Subsequent std devs in excess of 0.4 in several channels indicates that the bed is about to reach the point of no return and the reactor should be shut down.

For optimum operation, the ratio of $C_2H_4$ to HCl is adjusted so that the actual "ethylene efficiency" $C_2H_4Eff$ is as close to the theoretical maximum $(C_2H_4Eff)Max$ as possible. The $C_2H_4Eff$ is defined as the amount (moles) of ethylene dichloride (EDC) made, divided by the total amount (moles) of ethylene fed. The EDC is measured by analysis of the effluent from the reactor. The theoretical maximum ethylene efficiency is defined as the ratio of EDC which would theoretically be made for the particular ratio of ethylene to HCl in the fed to the reactor. This ratio of $C_2H_4:HCl$ is generally about 0.95.

Figure 2:
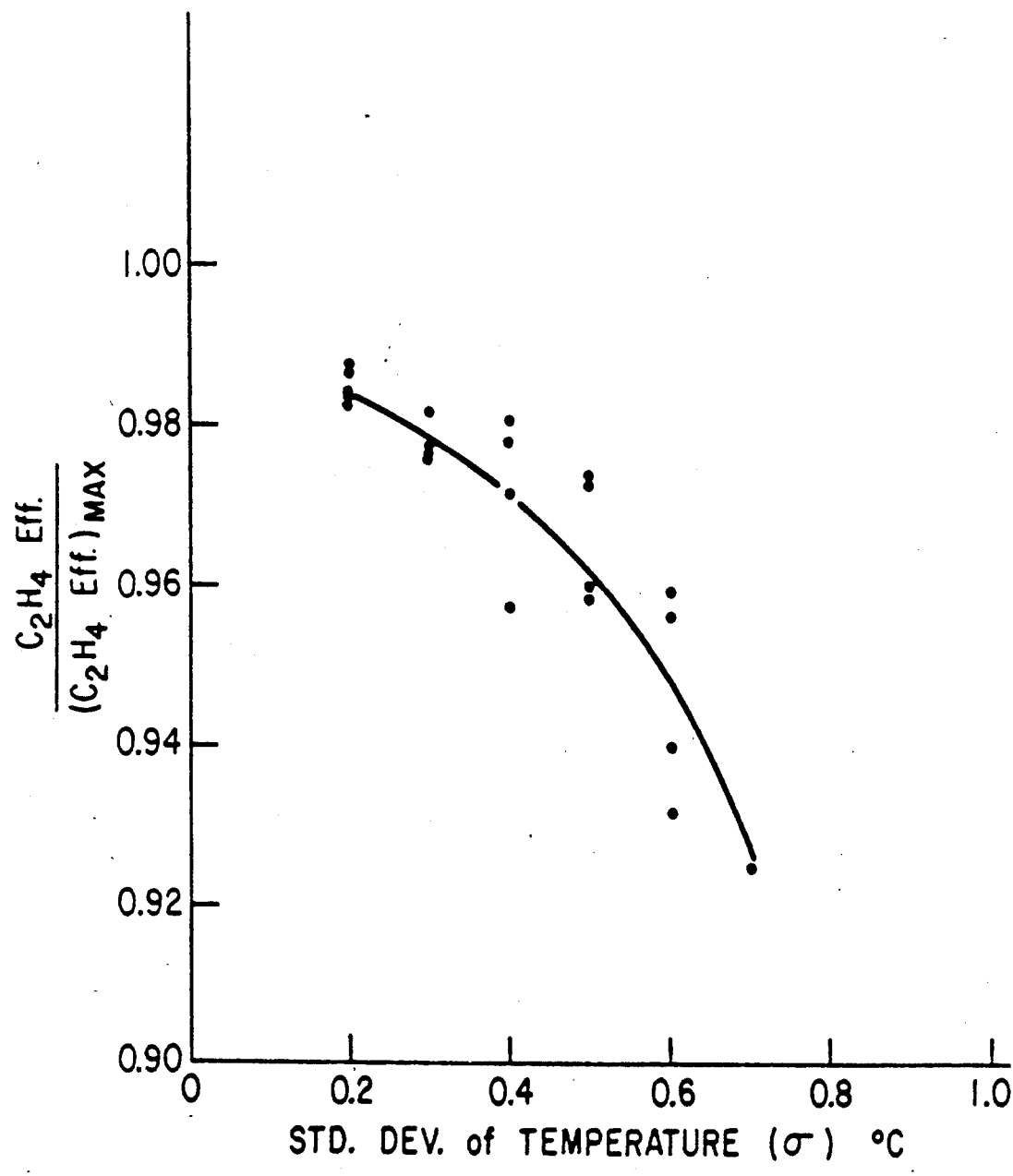
FIG. 2 is a plot of standard deviation (std dev) of temperature measured by at least one, and preferably several controlling thermocouples in the reactor, against the ratio of Ethylene Efficiency:Maximum Ethylene Efficiency.

In FIG. 2 the ratio of $C_2H_4Eff/(C_2H_4Eff)Max$ is plotted as a function of std dev of temperature. The points on the graph indicate the quality of fluidization as a function of the fluctuations in temperature. It is evident that the ratio begins to decrease when the std dev exceeds about 0.4, but is consistently above 0.97 when the ratio is less than 0.4.

Control means are provided which is responsive to the magnitude of the std dev, so that when a value of 0.4 is registered, the amount of ethylene fed is increased to decrease the value.

***************************************************************
*******************BEGIN DATA LOG******************

| MIN/CHN | 1 | 2 | 3 | 4 | 5 | 6 |
|---|---|---|---|---|---|---|
| 15.2 | 755.427 | 197.039 | 197.203 | 195.636 | 197.717 | 366.007 |
|  | 0.003 | 7.867 | 7.901 | 8.364 | 8.638 | 360.995 |
| 45.4 | 660.607 | 227.152 | 227.316 | 227.703 | 228.319 | 186.967 |
|  | 128.446 | 4.126 | 4.114 | 4.443 | 4.001 | 8.256 |
| 75.6 | 398.377 | 229.271 | 229.504 | 230.143 | 230.488 | 203.027 |
|  | 165.952 | 0.094 | 0.104 | 0.129 | 0.120 | 2.502 |
| 106.1 | 396.336 | 229.393 | 229.486 | 230.100 | 230.410 | 207.323 |
|  | 178.121 | 1.000 | 0.164 | 0.182 | 0.177 | 0.459 |

************************************************************
***************BEGIN DATA LOG***************
************************************************************

| MIN/CHN | 1 | 2 | 3 | 4 | 5 | 6 |
|---|---|---|---|---|---|---|
| 136.3 | 533.100 | 229.359 | 229.622 | 230.199 | 230.651 | 208.129 |
|  | 209.429 | 0.098 | 0.120 | 0.105 | 0.174 | 0.139 |
| 166.4 | 505.514 | 229.486 | 229.852 | 230.328 | 231.033 | 208.314 |
|  | 286.964 | 1.232 | 1.553 | 1.192 | 1.057 | 0.274 |
| 196.6 | 442.414 | 227.708 | 227.921 | 228.376 | 229.327 | 208.632 |
|  | 304.278 | 1.887 | 1.852 | 2.019 | 1.812 | 0.255 |
| 227.1 | 354.820 | 229.202 | 229.535 | 230.081 | 231.125 | 209.264 |
|  | 289.886 | 0.153 | 0.164 | 0.177 | 0.975 | 0.518 |
| 257.4 | 400.284 | 229.132 | 229.531 | 230.101 | 230.954 | 210.501 |
|  | 164.698 | 0.119 | 0.122 | 0.140 | 0.209 | 0.208 |
| 287.4 | 65.695 | 229.140 | 229.562 | 230.112 | 231.053 | 211.009 |
|  | 508.666 | 0.115 | 0.143 | 0.148 | 0.158 | 0.106 |
| 317.6 | −1460.242 | 229.065 | 229.509 | 230.120 | 230.986 | 211.089 |
|  | 187.597 | 0.115 | 0.135 | 0.141 | 0.175 | 0.075 |
| 347.8 | −1527.130 | 229.001 | 229.482 | 230.213 | 230.943 | 211.064 |
|  | 10.628 | 0.163 | 0.184 | 1.055 | 0.168 | 0.069 |
| 378.1 | −1534.679 | 229.012 | 229.469 | 230.111 | 230.955 | 211.113 |
|  | 6.456 | 0.144 | 0.149 | 0.165 | 0.207 | 0.102 |
| 408.4 | −1540.518 | 229.133 | 229.617 | 230.225 | 231.043 | 211.243 |
|  | 5.835 | 0.150 | 0.155 | 0.153 | 0.184 | 0.101 |
| 438.6 | −1545.434 | 229.107 | 229.568 | 230.212 | 231.043 | 211.295 |
|  | 7.398 | 0.120 | 0.139 | 0.156 | 0.205 | 0.070 |
| 468.8 | −1550.583 | 229.151 | 229.620 | 230.256 | 231.156 | 211.338 |
|  | 9.292 | 0.090 | 0.124 | 0.134 | 0.164 | 0.056 |
| 499.1 | −1559.034 | 229.144 | 229.607 | 230.254 | 231.166 | 211.351 |
|  | 12.286 | 0.155 | 0.168 | 0.182 | 0.200 | 0.072 |
| 529.3 | −1558.201 | 229.189 | 229.515 | 230.168 | 231.095 | 211.330 |
|  | 4.938 | 0.952 | 0.205 | 0.238 | 0.253 | 0.064 |
| 559.3 | −1156.023 | 229.097 | 229.572 | 230.228 | 231.120 | 211.329 |
|  | 747.493 | 0.148 | 0.160 | 0.166 | 0.219 | 0.061 |
| 589.3 | 330.198 | 229.110 | 229.700 | 230.183 | 231.143 | 211.474 |
|  | 200.105 | 0.186 | 0.957 | 0.216 | 0.187 | 0.986 |
| 619.3 | 183.773 | 229.017 | 229.505 | 230.143 | 231.110 | 211.350 |
|  | 261.183 | 0.189 | 0.189 | 0.203 | 0.222 | 0.062 |

************************************************************
* CONTINUED ON NEXT PAGE 192 ARGO II 0 SEQ NO *
************************************************************

192 ARGO II 0 SEQ NO DATE 2 23 86 REACTOR 1 PAGE 4
************************************************************

| MIN/CHN | 1 | 2 | 3 | 4 | 5 | 6 |
|---|---|---|---|---|---|---|
| 1402.9 | −1518.338 | 229.164 | 229.520 | 230.107 | 230.631 | 207.806 |
|  | 7.233 | 0.174 | 0.182 | 0.170 | 0.209 | 0.079 |
| 1432.9 | −1524.557 | 229.130 | 229.453 | 230.047 | 230.602 | 207.624 |
|  | 10.038 | 0.133 | 0.118 | 0.146 | 0.184 | 0.081 |
| 1462.9 | −1531.651 | 229.159 | 229.487 | 230.084 | 230.622 | 207.584 |
|  | 7.956 | 0.124 | 0.120 | 0.162 | 0.169 | 0.077 |
| 1493.1 | −1537.182 | 229.197 | 229.543 | 230.296 | 230.707 | 207.535 |
|  | 8.627 | 0.107 | 0.118 | 1.033 | 0.147 | 0.053 |
| 1523.3 | −1547.828 | 229.141 | 229.516 | 230.129 | 230.620 | 207.567 |
|  | 6.504 | 0.193 | 0.190 | 0.187 | 0.192 | 0.158 |
| 1553.4 | −1553.336 | 229.160 | 229.496 | 230.071 | 230.664 | 207.503 |
|  | 7.159 | 0.136 | 0.138 | 0.144 | 0.145 | 0.056 |
| 1583.4 | −1557.142 | 229.152 | 229.476 | 230.095 | 230.597 | 207.618 |
|  | 4.555 | 0.121 | 0.138 | 0.162 | 0.151 | 0.079 |
| 1613.4 | −1557.578 | 229.155 | 229.473 | 230.117 | 230.703 | 207.714 |
|  | 4.672 | 0.103 | 0.121 | 0.136 | 1.001 | 0.095 |
| 1643.4 | −1561.236 | 229.153 | 229.470 | 230.096 | 230.763 | 207.911 |
|  | 5.878 | 0.181 | 0.191 | 0.193 | 1.077 | 0.310 |
| 1673.4 | −1562.688 | 229.280 | 229.598 | 230.204 | 230.625 | 208.136 |
|  | 8.443 | 0.164 | 0.167 | 0.175 | 0.174 | 0.062 |
| 1703.4 | −1564.093 | 229.370 | 229.564 | 230.158 | 230.565 | 208.001 |
|  | 10.955 | 0.972 | 0.175 | 0.171 | 0.156 | 0.095 |
| 1733.4 | −1569.021 | 229.162 | 229.436 | 230.053 | 230.430 | 207.689 |
|  | 11.130 | 0.146 | 0.155 | 0.167 | 0.140 | 0.162 |

************************************************************
***************BEGIN DATA LOG***************
************************************************************

| MIN/CHN | 1 | 2 | 3 | 4 | 5 | 6 |
|---|---|---|---|---|---|---|
| 1763.4 | −1576.871 | 229.256 | 229.538 | 230.146 | 230.509 | 207.524 |
|  | 15.107 | 0.164 | 0.171 | 0.191 | 0.162 | 0.064 |
| 1793.4 | −1581.400 | 229.268 | 229.542 | 230.148 | 230.527 | 207.541 |
|  | 26.720 | 0.120 | 0.141 | 0.155 | 0.151 | 0.138 |
| 1823.4 | −1563.545 | 229.326 | 229.583 | 230.208 | 230.551 | 207.736 |
|  | 11.141 | 0.140 | 0.151 | 0.161 | 0.145 | 0.133 |
| 1853.4 | −1539.569 | 229.306 | 229.566 | 230.195 | 230.555 | 208.063 |
|  | 10.372 | 0.139 | 0.145 | 0.154 | 0.154 | 0.075 |
| 1883.4 | −1520.747 | 229.216 | 229.609 | 230.109 | 230.491 | 208.078 |
|  | 31.502 | 0.145 | 1.001 | 0.166 | 0.160 | 0.073 |
| 1913.4 | −1520.591 | 229.278 | 229.543 | 230.200 | 230.692 | 208.184 |
|  | 7.293 | 0.211 | 0.210 | 0.233 | 1.048 | 0.100 |
| 1943.4 | −1523.682 | 229.299 | 229.580 | 230.268 | 230.627 | 208.142 |
|  | 32.414 | 0.165 | 0.165 | 0.162 | 0.144 | 0.061 |
| 1973.4 | −1521.919 | 229.213 | 229.739 | 230.224 | 230.634 | 208.102 |
|  | 6.424 | 0.178 | 1.398 | 0.194 | 0.216 | 0.057 |
| 2003.4 | −1524.345 | 229.111 | 229.328 | 230.372 | 230.672 | 208.117 |
|  | 10.238 | 0.217 | 0.216 | 1.103 | 0.190 | 0.055 |
| 2033.4 | −1523.175 | 229.230 | 229.454 | 230.190 | 231.013 | 208.099 |
|  | 6.614 | 0.501 | 0.473 | 0.466 | 0.471 | 0.060 |
| 2063.4 | −1532.166 | 229.646 | 230.039 | 230.193 | 231.701 | 208.113 |
|  | 9.764 | 0.312 | 0.986 | 0.442 | 0.233 | 0.060 |
| 2093.4 | −1532.120 | 229.347 | 229.552 | 230.228 | 231.317 | 208.091 |
|  | 6.833 | 0.826 | 0.799 | 0.911 | 0.743 | 0.071 |
| 2123.4 | −1530.491 | 228.787 | 229.024 | 230.265 | 231.160 | 208.059 |
|  | 7.064 | 0.606 | 0.577 | 0.400 | 0.344 | 0.071 |

************************************************************
************************************************************

I claim:

1. In a fluid-bed reactor operating at elevated temperature and containing a finely divided catalyst which catalyzes a reaction of gaseous reactants which reaction changes the viscosity of said catalyst at operating conditions as a function of the ratio of said reactants, the improvement comprising, at least one thermocouple means, located at a preselected location within said bed, including a sheath having a diameter no greater than 0.5 inch and adapted to measure fluctuations in the range from about 0.1° F. to about 0.5° F., of the temperature at said location a plurality of times each minute; a means of converting analog temperature signal to a digital signal; means for computing an average temperature at said location during a predetermined period of time; means for quantifying the quality of fluidization of said catalyst by computing the standard deviation of temperature at said location said predetermined period of time; and, means for controlling the ratio of said reactants to lower said standard deviation below a preselected numerical value to increase the quality of fluidization of said catalyst.

2. The fluid-bed reactor of claim 1 wherein said gaseous reactants are ethylene, hydrochloric acid and oxygen, said catalyst is a supported catalyst on which is deposited at least one element selected from the group consisting of elements of Groups I, V, VI and VIII of the Periodic Table and compounds thereof, in the presence of which supported catalyst oxyhydrochlorination of monoolefin occurs which increases stickiness of said catalyst, and said means to control said ratio adjusts the ratio of ethylene to hydrochloric acid while maintaining an excess of oxygen.

* * * * *